US008263576B2

(12) United States Patent
Pagano et al.

(10) Patent No.: US 8,263,576 B2
(45) Date of Patent: Sep. 11, 2012

(54) NON-NATURAL SPHINGOLIPID ANALOGS AND USES THEREOF

(75) Inventors: Richard E. Pagano, Rochester, MN (US); Robert Bittman, Roslyn Heights, NY (US); David L. Marks, Rochester, MN (US); Hirohito Kita, Rochester, MN (US); Ramandeep S. Takhter, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 665 days.

(21) Appl. No.: 11/839,024

(22) Filed: Aug. 15, 2007

(65) Prior Publication Data

US 2008/0064645 A1 Mar. 13, 2008

Related U.S. Application Data

(60) Provisional application No. 60/838,024, filed on Aug. 15, 2006, provisional application No. 60/908,903, filed on Mar. 29, 2007.

(51) Int. Cl.
*A61K 31/715* (2006.01)
(52) U.S. Cl. .......................... 514/53; 536/17.9
(58) Field of Classification Search ................. 536/17.9; 514/25, 61, 53
See application file for complete search history.

(56) References Cited

U.S. PATENT DOCUMENTS

| | | | | |
|---|---|---|---|---|
| 5,936,076 | A * | 8/1999 | Higa et al. | 536/17.9 |
| 6,017,892 | A * | 1/2000 | Koezuka et al. | 514/25 |
| 6,204,002 | B1 * | 3/2001 | Iida et al. | 435/7.25 |
| 6,417,167 | B1 * | 7/2002 | Maruyama et al. | 514/25 |
| 6,747,010 | B2 * | 6/2004 | Taniguchi et al. | 514/25 |

OTHER PUBLICATIONS

Anderson et al., "Bound Simian Virus 40 Translocates to Caveolin-enriched Membrane Domains, and Its Entry Is Inhibited by Drugs that Selectively Disrupt Caveolae," *Mol. Biol. Cell*, 1996, 7:1825-1834.
Arias-Salgado et al., "Src kinase activation by direct interaction with the integrin β cytoplasmic domain," *Proc. Natl. Acad. Sci. USA*, 2003, 100(23):13298-13302.
Blattner and Kretzler, "Integrin-linked kinase in renal disease: connecting cell-matrix interaction to the cytoskeleton," *Curr. Opin. Nephrol. Hypertens*, 2005, 14:404-410.
Dagan et al., "Synthetic, non-natural sphingolipid analogs inhibit the biosynthesis of cellular sphingolipids, elevate ceramide and induce apoptotic cell death," *Biochim. Biophys. Acta*, 2003, 1633:161-169.
Faull and Ginsberg, "Inside-Out Signaling Through Integrins," *J. Am. Soc. Nephrol.*, 1996, 7:1091-1097.
Ferraccioli and Gremese, "Biological therapies in autoimmune chronic inflammatory diseases (ACIDs)," *Eur. Rev. Med. Pharmacol. Sci.*, 2006, 10:37-40.

Hansel et al., "An improved immunomagnetic procedure for the isolation of highly purified human blood eosinophils," *J. Immunol. Meth.*, 1991, 145:105-110.
IUPAC-IUB Commission on Biochemical Nomenclature. Abbreviated Nomenclature of Synthetic Polypeptides (Polymerized Amino Acids). Revised Recommendations (1971), *IUPAC-IUB Comm. Biochem. Nomenclature*, 1972, 11:942-944.
Liu and Bittman, "Synthesis of fluorescent lactosylceramide stereoisomers," *Chem. Phys. Lipids*, 2006, 142:58-69.
Luque et al., "Activated Conformations of Very Late Activation Integrins Detected by a Group of Antibodies (HUTS) Specific for a Novel Regulatory Region (355-425) of the Common β1 Chain," *J. Biol. Chem.*, 1996, 271(19):11067-11075.
Marks et al., "Use of fluorescent sphingolipid analogs to study lipid transport along the endocytic pathway," *Methods*, 2005, 36:186-195.
Mineo and Anderson, "Potocytosis," *Histochem. Cell Biol.*, 2001, 116:109-118.
Norkin and Kuksin, "The caveolae-mediated sv40 entry pathway bypasses the golgi complex en route to the endoplasmic reticulum," *Virol. J.*, 2005, 2:38-43.
Pelkmans et al., "Caveolar endocytosis of simian virus 40 reveals a new two-step vesicular-transport pathway to the ER," *Nature Cell Biol.*, 2001, 3:473-483.
Sharma et al., "The Glycosphingolipid, Lactosylceramide, Regulates β₁-Integrin Clustering and Endocytosis," *Cancer Res.*, 2005, 65:8233-8241.
Sharma et al., "Selective Stimulation of Caveolar Endocytosis by Glycosphingolipids and Cholesterol," *Mol. Biol. Cell*, 2004, 15:3114-3122.
Sheremata et al., "The Role of Alpha-4 Integrin in the Aetiology of Multiple Sclerosis. Current Knowledge and Therapeutic Implications," *CNS Drugs*, 2005, 19(11):909-922.
Singh et al., "Using Fluorescent Sphingolipid Analogs to Study Intracellular Lipid Trafficking," *Curr. Prot. Cell Biol.*, 2007, Sections 24.1.1-24.1.19.
Singh et al., "Caveolar Endocytosis and Microdomain Association of a Glycosphingolipid Analog Is Dependent on Its Sphingosine Stereochemistry," *J. Biol. Chem.*, 2006, 281(41):30660-30668.
Singh et al., "Inhibition of caveolar uptake, SV40 infection, and β1-integrin signaling by a nonnatural glycosphingolipid stereoisomer," *J. Cell Biol.*, 2007, 176(7):895-901.
Singh et al., "Selective Caveolin-1-dependent Endocytosis of Glycosphingolipids," *Mol. Biol. Cell*, 2003, 14:3254-3265.
Stang et al., "Major Histocompatibility Complex Class I Molecules Mediate Association of SV40 with Caveolae," *Mol. Biol. Cell*, 1997, 8:47-57.
Tsai et al., "Gangliosides are receptors for murine polyoma virus and SV40," *EMBO J.*, 2003, 22(17):4346-4355.

(Continued)

*Primary Examiner* — Elli Peselev
(74) *Attorney, Agent, or Firm* — Fish & Richardson P.C.

(57) ABSTRACT

This disclosure provides a composition useful for inhibiting caveolar endocytosis, plasma membrane microdomain formation, virus binding and infection, transmembrane signaling, and integrin function in cells. The composition is composed of non-natural analogs of sphingolipids, and may have applications in the treatment or amelioration of diseases associated with caveolar endocytosis, plasma membrane microdomain formation, transmembrane signaling, and integrin function. Methods for making and using the described composition are also provided.

4 Claims, 7 Drawing Sheets

OTHER PUBLICATIONS

Upla et al., "Clustering Induces a Lateral Redistribution of α2β1 Integrin from Membrane Rafts to Caveolae and Subsequent Protein Kinase C-dependent Internalization," *Mol. Biol. Cell*, 2004, 15:625-636.

Venkataraman and Futerman, "Comparison of the metabolism of L-*erythro*- and L-*threo*-sphinganines and ceramides in cultured cells and in subcellular fractions," *Biochim. Biophys. Acta*, 2001, 1530:219-226.

Vijayan and Bray, "Molecular Mechanisms of Prothrombotic Risk Due to Genetic Variations in Platelet Genes: Enhanced Outside-In Signaling Through the Pro$^{33}$ Variant of Integrin $\beta_3$," *Exp. Biol. Med.*, 2006, 231(5):505-513.

* cited by examiner

A n' = 1 or 3 n = 1, 5, 7, or 9

Gal
Gal[β(1→4)]Glc
Glc[α(1→4)]Glc
Gal-Gal-Glc-
SO₄-Gal-
Gal-GalNAc-Gal-Glc-
           |
       NeuAc

GalCer
LacCer
MalCer
Globoside
Sulfatide
$GM_1$

B

NON-NATURAL SPHINGOLIPID ANALOGS AND USES THEREOF

CROSS REFERENCE TO RELATED APPLICATION

This application claims priority under 35 U.S.C. §119 to U.S. Ser. No. 60/838,024, filed Aug. 15, 2006 and U.S. Ser. No. 60/908,903, filed Mar. 29, 2007, the contents of which are incorporated by reference in their entirety.

The present invention was funded, in part, by the United States Public Health Service, Grant numbers GM-22942 and HL-083187; the United States government has certain rights in this invention.

TECHNICAL FIELD

This disclosure relates to modulation of cellular functions, and more particularly to the use of a non-natural sphingolipid analog to inhibit caveolar endocytosis, plasma membrane microdomain formation, transmembrane signaling, and integrin function, e.g., for therapeutic uses.

BACKGROUND

Sphingolipids (SLs) can participate in a wide variety of cellular functions, including cell-cell interactions, cell growth and differentiation, and signal transduction. SLs can interact with cholesterol to form membrane microdomains, and data from many studies suggest that the plasma membrane (PM) SL and cholesterol composition may be tightly regulated. To achieve this regulation, cells must balance complex processes such as endocytosis, recycling, intracellular sorting, and metabolism of SLs.

Several clathrin-independent mechanisms of endocytosis have been identified and actively studied in mammalian cells. One well-studied clathrin-independent mechanism is uptake via caveolae—flask-shaped invaginations at the PM that are enriched in SLs and cholesterol and are associated with the protein, caveolin-1 (Cav1). Caveolae may be involved in the uptake and/or binding of certain viruses (e.g., SV40), toxins (e.g., cholera toxin B subunit (CtxB)), fungi, bacteria, SLs, integrins, and albumin in various cell types.

Membrane microdomains represent local regions of membranes that have a different overall composition from the bulk membrane and are thought to act as organizing centers to sequester particular lipids and proteins. Evidence for microdomains in various intracellular membranes comes from multiple approaches including "detergent insolubility" of membrane components, crosslinking of membrane proteins and lipids, biophysical studies of constrained lateral diffusion in membranes, energy transfer measurements to demonstrate "clustering" of labeled proteins in membranes, and EM studies to visualize local "enrichment" of particular proteins or lipids on membranes. Microdomain formation is thought to play a role in processes such as intracellular sorting and membrane signaling events. Caveolae (enriched in glycosphingolipids (GSLs) and cholesterol) are considered to be one type of PM microdomain.

Integrins are a family of αβ heterodimeric membrane proteins at the PM which bind to extracellular matrix proteins and cell surface ligands, and are responsible for many types of cell adhesion events. Some integrins are internalized via caveolae or are present in lipid-enriched microdomains.

SUMMARY

Provided herein are compounds, compositions containing the compounds, and methods of use of the compounds useful to prevent formation of PM domains and inhibit caveolar endocytosis, transmembrane signaling, and integrin function. Also provided are methods of treatment or amelioration of one or more symptoms of diseases and disorders associated with PM domain formation, caveolar endocytosis, transmembrane signaling, and integrin function. Such diseases and disorders include, but are not limited to, infection by various pathogens (e.g., certain bacteria, fungi, and viruses), cancer, multiple sclerosis, prothrombotic risk, ulcerative colitis, and renal disease.

In one embodiment, the compounds for use in the compositions and methods provided herein have Formula I:

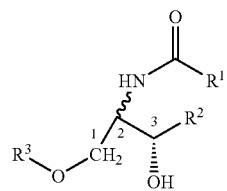

where the stereochemistry at carbons 2 and 3 can be (2S,3S) (i.e., L-threo) or (2R,3S) (i.e., L-erythro); $R^1$ is $C_{1-25}$ alkyl, $C_{2-25}$ alkenyl, $C_{2-25}$ alkynyl, $C_{2-25}$ aralkyl, $C_{2-25}$ heteroaralkyl, $(C_{1-20}$ alkyl)X, $(C_{2-20}$ alkenyl)X; or $(C_{2-20}$ alkynyl)X; X is a fluorophore; $R^2$ is $C_{1-25}$ alkyl, $C_{2-25}$ alkenyl, $C_{2-25}$ alkynyl, $C_{2-25}$ aralkyl, or $C_{2-25}$ heteroaralkyl; $R^3$ comprises carbohydrates and substituted choline derivatives. For example, carbohydrates may include monosaccharides, disaccharides, oligosaccharides, carbohydrates containing one or more (e.g., 1, 2, 3, or 4) sialic acid residues, and carbohydrates containing sulfate esters. In certain cases, the anomeric carbon of the carbohydrate-containing group(s) can be linked to the sphingolipid backbone via a β-anomeric bond. In addition, $R^3$ may be selected from the group consisting of the formulae:

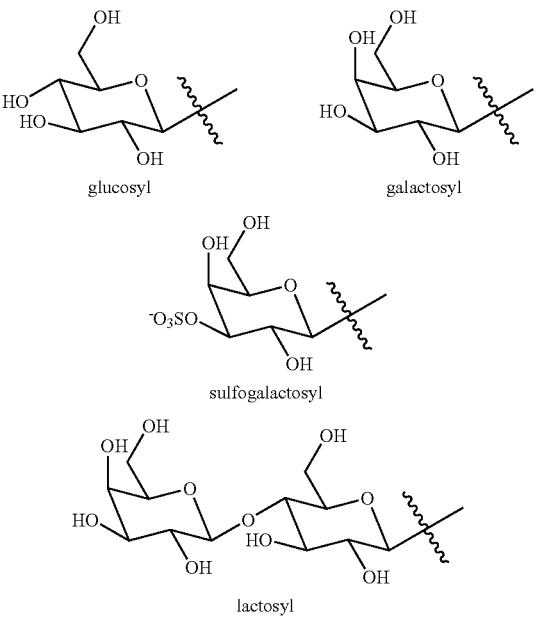

-continued

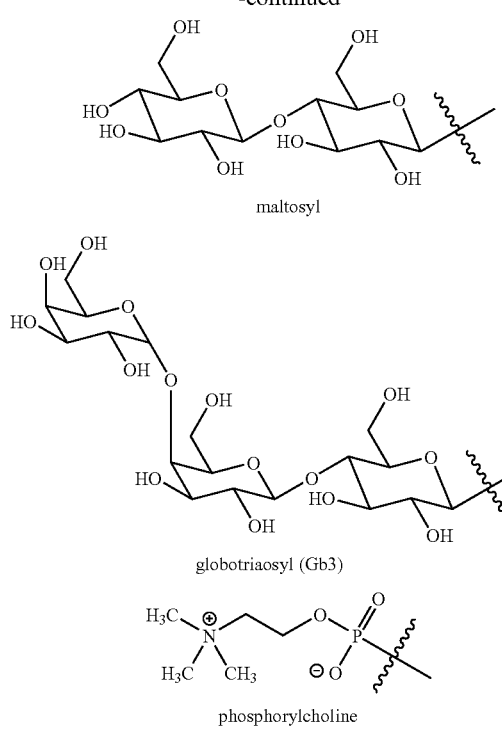

maltosyl globotriaosyl (Gb3)

phosphorylcholine

In some embodiments, $R^1$ is a $C_{6-22}$ alkyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, and $C_{22}$ alkyl). In other embodiments, $R^1$ is a $(C_{1-5}$ alkyl)X. In further embodiments, X is selected from boron dipyrromethenedifluoride (BODIPY), 7-(4-nitrobenzo-2-oxa-1,3-diazole) (NBD), dimethylaminonaphthalenesulfonate (Dansyl), pyrene, rhodamine, courmarin, or fluorescein. In some instances, X is BODIPY. In certain embodiments, $R^2$ is a $C_{5-20}$ alkyl (e.g., $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl). In other embodiments, $R^3$ is a group of the formula:

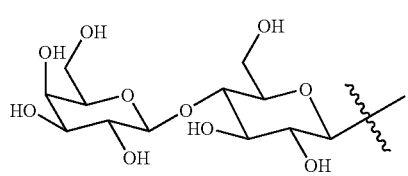

In still further embodiments, the compound of Formula I is β-D-lactosyl-N-octanoyl-L-threo-sphingosine or C8-L-threo-lactosylceramide (C8-LT-LacCer).

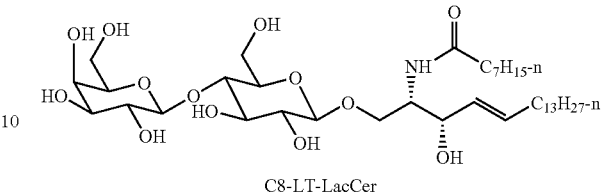

C8-LT-LacCer

In another embodiment, the compound of Formula I is C8-L-threo-galactosylceramide (C8-LT-GalCer).

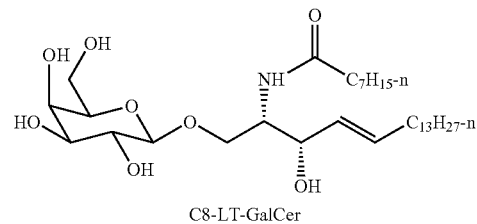

C8-LT-GalCer

In other embodiments, the compound of Formula I is C8-L-threo-globoside (C8-LT-Gb3).

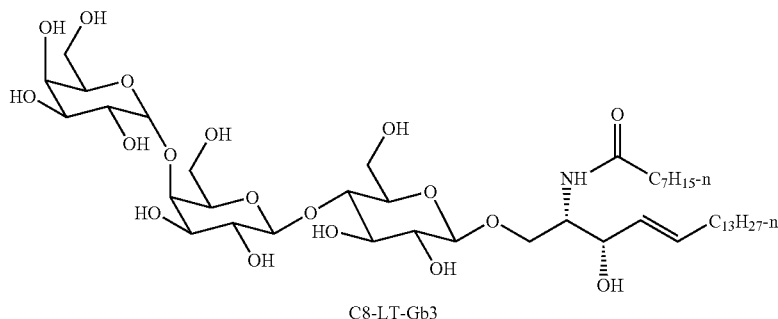

C8-LT-Gb3

In some embodiments, the compound of Formula I is C8-L-threo-sphingomyelin (C8-LT-SM).

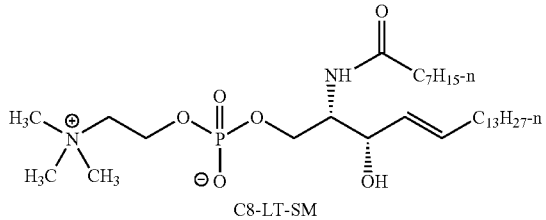

C8-LT-SM

In further embodiments, the compound of Formula I is C6-L-threo-sphingomyelin (C6-LT-SM).

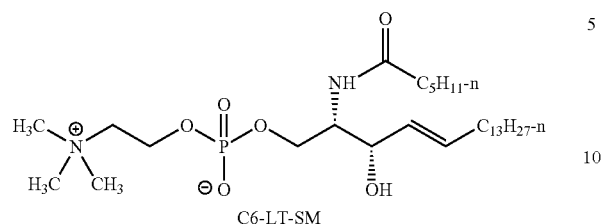

C6-LT-SM

In one embodiment, the compound of Formula I is C8-L-threo-monosialohexosylganglioside (C8-LT-GM$_4$).

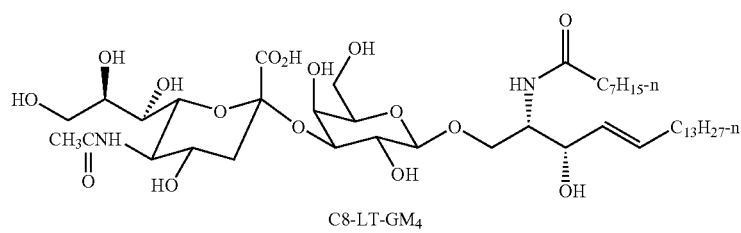

C8-LT-GM$_4$

In certain embodiments, the compound of Formula I is C8-L-threo-monosialodihexosylganglioside (C8-LT-GM$_3$).

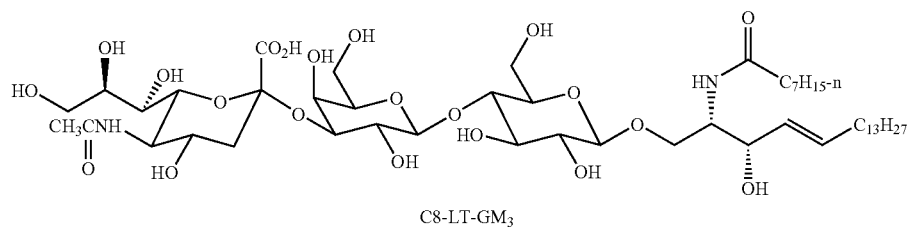

C8-LT-GM$_3$

In some embodiments, the compound of Formula I is C8-L-threo-monosialotetrahexosylganglioside (C8-LT-GM$_1$).

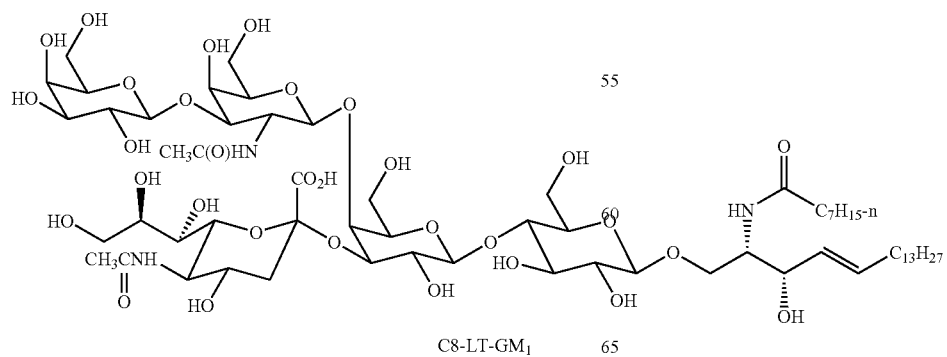

C8-LT-GM$_1$

In another embodiment, the compound of Formula I is C5-BODIPY-L-threo-lactosylceramide (C5-BODIPY-LT-LacCer).

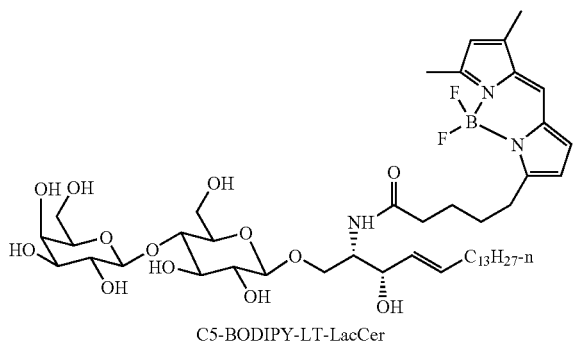

C5-BODIPY-LT-LacCer

Also provided are pharmaceutically acceptable derivatives, including salts, esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Previous studies have demonstrated that incubation of human skin fibroblasts (HSFS) with glycosphingolipids (GSLs) stimulates endocytosis of several caveolar markers (see, e.g., Sharma, D. K. et al., *Molec. Biol. Cell* 2004, 15, 3114 and Sharma, D. K. et al., *Cancer Res.* 2005, 65, 1). For example, treatment of HSFs with a natural lactosylceramide or an analog having an 8 carbon fatty acid and the natural, D-erythro, configuration of ceramide (referred to as C8-DE-LacCer herein) not only stimulated caveolar endocytosis, but also promoted formation of PM microdomains, and induced clustering and activation of β1-integrin within those domains. Treatment with exogenous SLs has thus been postulated to promote the formation of PM microdomains, which in turn induce the clustering and "activation" of certain transmembrane proteins, and a subsequent "signaling cascade" that promotes caveolar endocytosis (see FIG. 1). For example, within these microdomains the activation of β1-integrin stimulates src kinase (phosphorylated at Y416), a result which is observed when HSFs are incubated with C8-DE-LacCer. In addition to stimulation of the β1-integrin in fibroblast cells, work with human eosinophils has shown that treatment with C8-DE-LacCer in combination with Interleukin-5 (IL-5) stimulated β2-integrins, results in increased superoxide production.

The present disclosure demonstrates, on the other hand, that a non-natural GSL, a compound of Formula I having the non-natural L-threo configuration of ceramide (e.g., C8-LT-LacCer), may prevent PM microdomain formation and inhibit both transmembrane signaling (e.g., integrin signaling or function) and caveolar endocytosis. In certain embodiments, a compound of Formula I may selectively block β1-integrin clustering and activation within plasma membrane microdomains in cells (e.g., HSFs). This inhibition can also occur in the presence of a kinase activating antibody. In other embodiments, a compound of Formula I may inhibit β2-integrins, which may result in the inhibition of superoxide production in combination with IL-5 treatment in cells (e.g., human eosinophils).

Given the above, the compound of Formula I may be used to treat diseases in a mammal in which caveolar endocytosis, plasma membrane microdomain formation, transmembrane signaling, or integrin function are implicated. For example, inhibiting caveolar endocytosis may result in the inhibition of infection and/or binding of a cell by certain bacterium, fungus, or virus species (e.g., SV40 virus). In other embodiments, the compound of Formula I may be able to treat diseases associated with integrin function (e.g., inflammatory diseases, cancer, multiple sclerosis, prothrombotic risk, ulcerative colitis, and renal disease).

In a further embodiment, the compound of Formula I may be used as a tool in which to determine whether or not a test compound is capable of restoring an inhibited function (e.g., caveolar endocytosis or plasma membrane microdomain formation) by contacting a cell with a compound of Formula I and the test compound. In some embodiments, the cell is first contacted with the compound of Formula I, while in other embodiments the test compound makes the initial contact with the cell. In certain embodiments, a cell is contacted with a compound of Formula I and the level of a cellular function (e.g., caveolar endocytosis) is determined. The cell is then contacted with the test compound and the level of the cellular function is again measured. Finally, the results of the two measurements are compared to determine whether or not the cellular function has increased or decreased between its exposure to the compound of Formula I and the test compound. In some embodiments, each of the measurements may be compared to the results obtained from a control cell (e.g., a cell contacted with a derivative of the compound of Formula I having D-erythro or D-threo stereochemistry). For example, a test compound may be able to promote infection and/or binding of a cell by a virus (e.g., to aid in gene therapy) in the presence of a compound of Formula I. In some embodiments, a change in the cellular function may indicate that the test compound is capable of overcoming the modulation brought forth by the compound of Formula I; while in other embodiments, a change in the cellular function may instead indicate that a process other than the one being measured is operative for the test compound (e.g., the test compound may be able to enter the cell through a route other than caveolar endocytosis).

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4a: HSFs were serum-starved for 2-3 hrs and then either untreated (panel 1, Control) or incubated with a stimulating β1-integrin IgG (panel 2; β1-stim) or with the LacCer isomers (panels 3 & 4) for 30 min at 10° C. All samples were then warmed for 30 sec at 37° C., fixed and stained with HUTS-4 Ab that recognizes β1-integrin in its active conformation. Note the absence of β1-integrin activation in cells pretreated with C8-LT-LacCer. Quantitation in FIG. 4b was by image analysis (n≧10 cells/condition; 3 independent experiments). Bars, 10 µm.

DETAILED DESCRIPTION

Definitions

Figure 1:
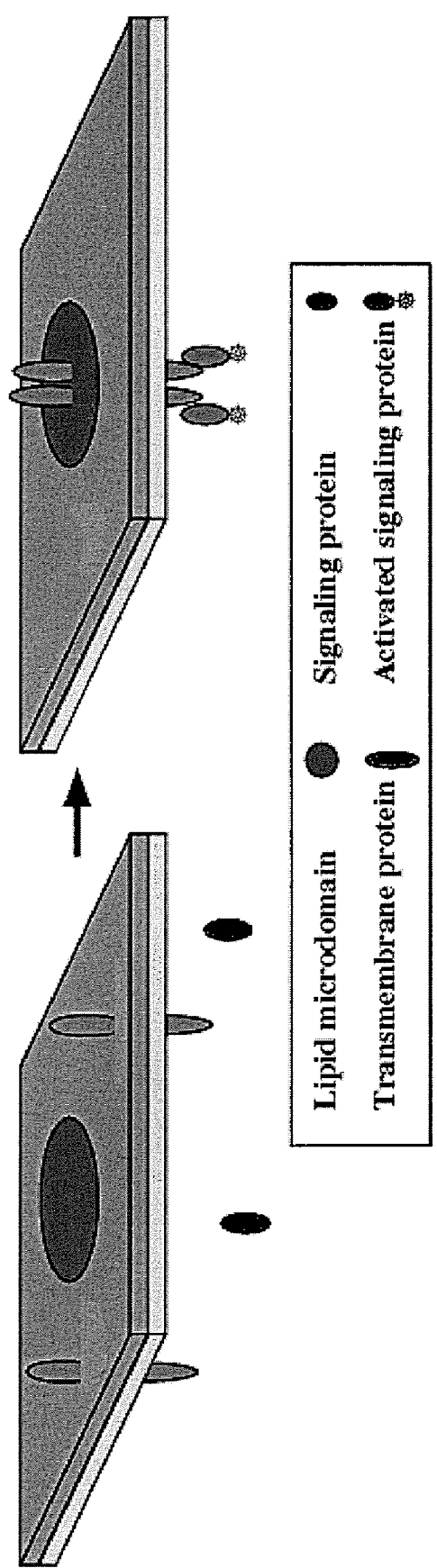
FIG. 1 is a model demonstrating stimulation of caveolar endocytosis by exogenous SLs (including exogenous GSLs). Exogenous GSLs or cholesterol promote formation of microdomains (circle in center). Transmembrane proteins (e.g., β1-integrins, tetraspanins, or other molecules) cluster in these microdomains and undergo conformational changes, leading to signaling via src and perhaps other kinases that are required for caveolar endocytosis.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, modulating means any manner in which one or more cellular functions are inhibited, suppressed, modified, moderated, restored, increased or decreased in activity or otherwise altered as compared to a control or other test cell. Modulation also encompasses any change which is initiated by the administration of any pharmaceutical containing the composition described herein, such as use for treating diseases or disorders where the modulation of cellular function is implicated.

As used herein, "alkyl," "alkenyl" and "alkynyl" carbon chains, if not specified, contain from 1 to 25 carbons, or 1 or 2 to 22 carbons (e.g., 8-16, 5-15, 2-8, 6-12, 8-22, 6-22 and 10-18), and are straight or branched, substituted or unsubstituted. Alkenyl carbon chains of from 2 to 25 carbons, in certain embodiments, contain 1 to 8 double bonds and alkenyl carbon chains of 2 to 22 carbons, in certain embodiments, contain 1 to 5 double bonds. Alkynyl carbon chains of from 2 to 25 carbons, in certain embodiments, contain 1 to 8 triple bonds, and the alkynyl carbon chains of 2 to 22 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). Substitutions may include, but are not limited to, halo, pseudohalo, alkyl, alkoxy, cycloalkyl, aryl, heteroaryl, amino, hydroxy, alkoxycarbonyl, hydroxycarbonyl, and fluorescent fatty acids, for example, dipyrromethene boron difluoride (BODIPY), 7-nitrobenz-2-oxa-1,3-diazol-4-yl (NBD), dimethylaminonaphthalenesulfonate (Dansyl), pyrene, rhodamine, courmarin, or fluorescein.

As used herein, "aryl" refers to aromatic monocyclic or multicyclic groups containing from 6 to 19 carbon atoms. Aryl groups include, but are not limited to groups such as unsubstituted or substituted phenyl and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "halo" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "cycloalkyl" refers to a saturated mono- or multi-cyclic ring system, in certain embodiments of 3 to 10 carbon atoms, in other embodiments of 3 to 6 carbon atoms.

As used herein, "hydroxycarbonyl" refers to —COOH.

As used herein, "alkoxycarbonyl" refers to —C(O)OR in which R is alkyl, including lower alkyl.

As used herein, "alkoxy" refers to RO— in which R is alkyl, including lower alkyl. As used herein, "amino" refers to $H_2N$— and "hydroxyl" refers to HO—.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, pharmaceutically acceptable derivatives of a compound include salts, esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which caveolar endocytosis, PM microdomain formation, transmembrane signaling, or integrin function is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the abbreviations for any compounds or biological compositions, are, unless indicated otherwise, in accord with their common usage, recognized abbreviations, or the IUPAC-IUB Commission on Biochemical Nomenclature (see, (1972) *Biochem.* 11:942-944).

Compositions of Matter

This disclosure is directed to the use of non-natural sphingolipids, the compounds of Formula I, for the inhibition of caveolar endocytosis, plasma membrane microdomain formation, transmembrane signaling and integrin function, including for the treatment, prevention, or amelioration of a disease associated with these cellular functions. The disclosure demonstrates that certain SLs, including those with D-erythro or D-threo stereochemistry, may regulate caveolar endocytosis by inducing the clustering of integrins and other transmembrane (TM) proteins into PM domains, resulting in their activation and transmembrane signaling. The compounds of Formula I, on the other hand, prevent PM microdomain formation and inhibit integrin signaling and caveolar endocytosis. For example, in one embodiment, a compound of Formula I, C8-LT-LacCer, selectively blocks β1-integrin clustering and activation in HSFs, and may inhibit superoxide production in combination with IL-5 treatment in human eosinophils. Accordingly, the use of the compounds of Formula I can be extended to other cells types where inhibition of caveolar endocytosis, PM microdomain formation, transmembrane signaling and integrin function may have significant effects on inflammatory responses (e.g., asthma, allergy), cell migration and invasiveness (e.g., of cancerous or precancerous cells), and infection by certain bacteria, fungi, and viruses.

In one embodiment, the compounds for use in the compositions and methods provided herein have Formula I:

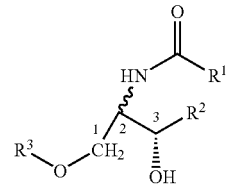

where the stereochemistry at carbons 2 and 3 can be (2S,3S) (i.e., L-threo), (2R,3S) (i.e., L-erythro), (2S,3R) (i.e., D-erythro), or (2R,3R) (i.e., D-threo); $R^1$ can be $C_{1-25}$ alkyl, $C_{2-25}$ alkenyl, $C_{2-25}$ alkynyl, $C_{2-25}$ aralkyl, $C_{2-25}$ heteroaralkyl, ($C_{1-20}$ alkyl)X, ($C_{2-20}$ alkenyl)X; or ($C_{2-20}$ alkynyl)X; X can be any fluorophore; $R^2$ can be $C_{1-25}$ alkyl, $C_{2-25}$ alkenyl, $C_{2-25}$ alkynyl, $C_{2-25}$ aralkyl, or $C_{2-25}$ heteroaralkyl.

In certain embodiments, $R^3$ can be a carbohydrate or substituted choline derivative. Examples of carbohydrates include monosaccharides (e.g., glucose, fructose, ribose, and galactose), disaccharides (e.g., sucrose, lactose, and maltose), oligosaccharides, gangliosides, carbohydrates containing one or more sialic acid residues (e.g., 1, 2, 3, or 4 sialic acid residues), and carbohydrates containing sulfate esters. In some embodiments, $R^3$ is selected from the group consisting of the formulae:

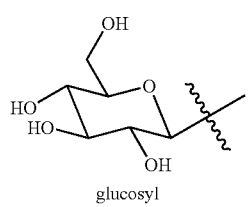
glucosyl

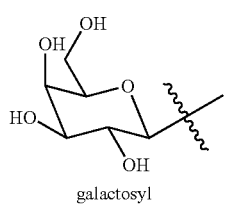
galactosyl

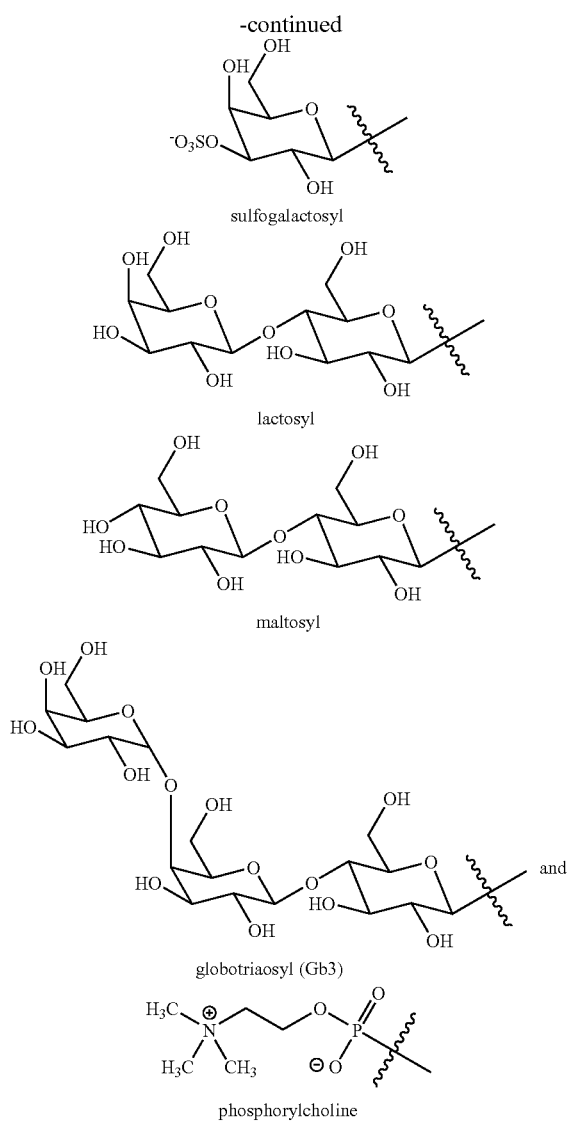

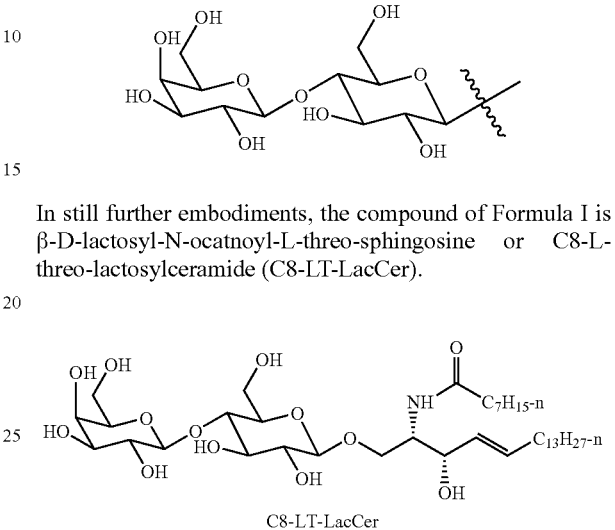

In further embodiments, $R^1$ is a $C_{1-25}$ alkyl (e.g., $C_{1-10}$, $C_{2-12}$, $C_{4-16}$, $C_{8-10}$, $C_{10-12}$, $C_{8-12}$, $C_{12-16}$, $C_{14-16}$, $C_{11-15}$, $C_{13-16}$, $C_{10-20}$, $C_{12-24}$, $C_{8-22}$, $C_{15-25}$, and $C_{18-24}$). In other embodiments, $R^1$ is a $C_{8-22}$ alkyl. In other embodiments, R1 is ($C_{1-5}$ alkyl)X. In further embodiments, X is selected from boron dipyrromethenedifluoride (BODIPY), 7-(4-nitrobenzo-2-oxa-1,3-diazole) (NBD), dimethylaminonaphthalenesulfonate (Dansyl), pyrene, rhodamine, courmarin, or fluorescein. In some instances, X is BODIPY. In certain embodiments, $R^2$ is a $C_{5-20}$ alkyl (e.g., $C_{5-10}$, $C_{6-12}$, $C_{5-7}$, $C_{10-15}$, $C_{6-9}$, $C_{8-14}$, $C_{11-15}$, $C_{10-20}$, $C_{12-18}$, $C_{14-20}$, $C_{17-19}$, and $C_{16-20}$). In some embodiments, $R^3$ is a group of the formula:

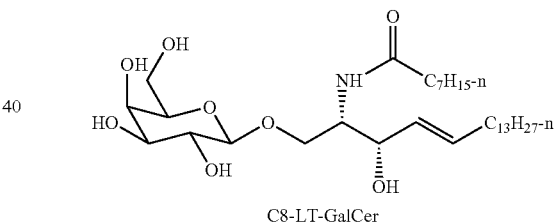

In still further embodiments, the compound of Formula I is β-D-lactosyl-N-ocatnoyl-L-threo-sphingosine or C8-L-threo-lactosylceramide (C8-LT-LacCer).

In other embodiments, the compound of Formula I is C8-L-erythro-lactosylceramide (C8-LE-LacCer). In another embodiment, the compound of Formula I is C8-L-threo-galactosylceramide (C8-LT-GalCer).

In certain embodiments, the compound of Formula I is C8-L-erythro-galactosylceramide (C8-LE-GalCer). In other embodiments, the compound of Formula I is C8-L-threo-globoside (C8-LT-Gb3).

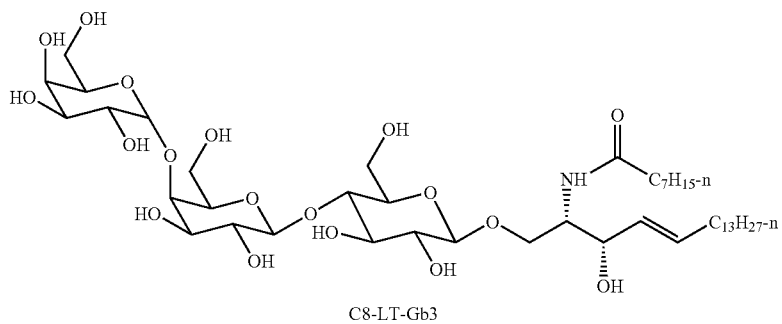

In further embodiments, the compound of Formula I is C8-L-erythro-globoside (C8-LE-Gb3). In some embodiments, the compound of Formula I is C8-L-threo-sphingomyelin (C8-LT-SM).

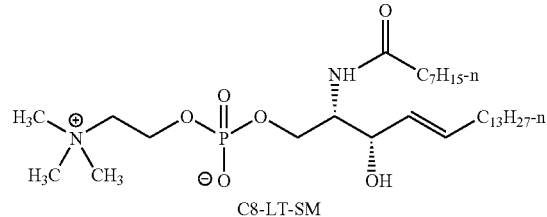

C8-LT-SM

In certain embodiments, the compound of Formula I is C8-L-erythro-sphingomyelin (C8-LE-SM). In further embodiments, the compound of Formula I is C6-L-threo-sphingomyelin (C6-LT-SM).

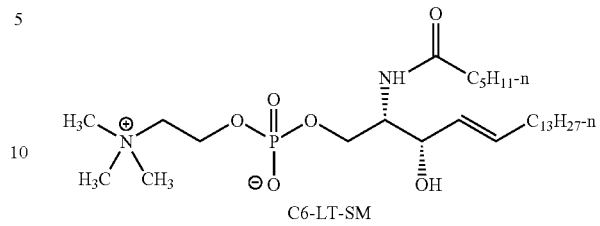

C6-LT-SM

In other embodiments, the compound of Formula I is C6-L-erythro-sphingomyelin (C6-LE-SM). In one embodiment, the compound of Formula I is C8-L-threo-monosialohexosylganglioside (C8-LT-GM$_4$).

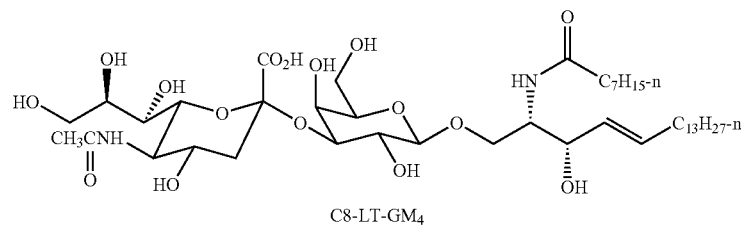

C8-LT-GM$_4$

In another embodiment, the compound of Formula I is C8-L-erythro-monosialohexosylganglioside (C8-LE-GM$_4$). In certain embodiments, the compound of Formula I is C8-L-threo-monosialodihexosylganglioside (C8-LT-GM$_3$).

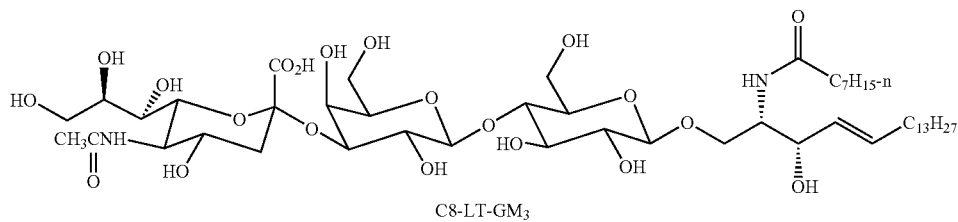

C8-LT-GM$_3$

In certain embodiments, the compound of Formula I is C8-L-erythro-monosialodihexosylganglioside (C8-LE-GM$_3$).
In some embodiments, the compound of Formula I is C8-L-threo-monosialotetrahexosylganglioside (C8-LT-GM$_1$).

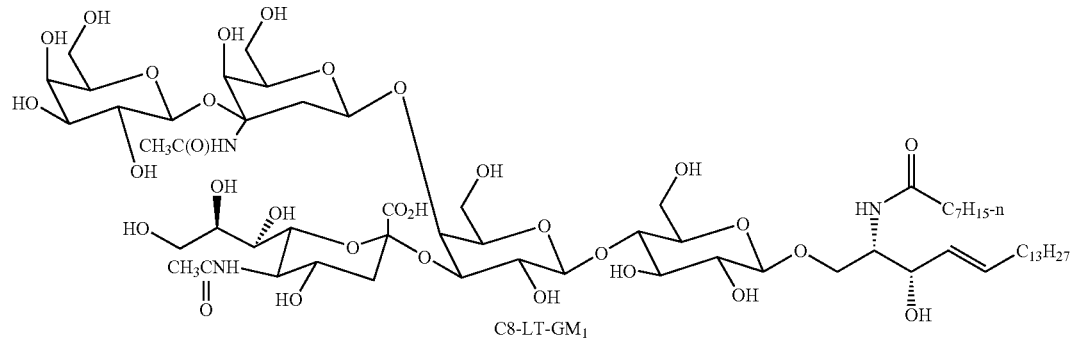

C8-LT-GM$_1$

In other embodiments, the compound of Formula I is C8-L-erythro-monosialotetrahexosylganglioside (C8-LE-GM$_1$). In another embodiment, the compound of Formula I is C5-BODIPY-L-threo-lactosylceramide (C5-BODIPY-LT-LacCer).

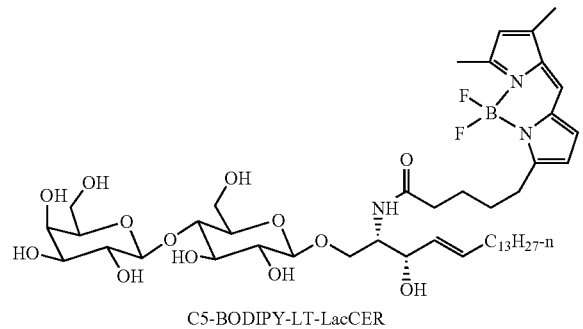

C5-BODIPY-LT-LacCER

In further embodiments, the compound of Formula I is C5-BODIPY-L-erythro-lactosylceramide (C5-BODIPY-DE-LacCer) or C5-BODIPY-D-threo-lactosylceramide (C5-BODIPY-LT-LacCer).

The compositions of this disclosure may be prepared by the procedure described by Liu, Y. et al. (see, Liu, Y. and Bittman, R. *Chem. Phys. Lipids* 2006, 142, 58.) In certain embodiments, the procedure may be modified as required to obtain the desired compounds. In one embodiment of the disclosure, the implementation of an appropriate acid may be used to obtain the correct substitution at R$^1$ (e.g., octanoic acid), various terminal alkynes may be used to account for the variation in R$^2$ (e.g., 1-pentadecyne), and the formula used at R$^3$ may be obtained through modification of reaction conditions, known to one of ordinary skill in the art, to obtain the appropriate configuration of the suitably activated glycosyl donor (e.g., trichloroacetimidate, molecular sieves and a solution of BF$_3$.Et$_2$O in CH$_2$Cl$_2$ stirred overnight to obtain the lactosyl functionality).

In some embodiments, the compositions provided herein may be further modified into a pharmaceutical composition, and may exist as a pharmaceutically acceptable salt or derivative. The pharmaceutical compositions provided herein contain therapeutically effective amounts of the compounds provided herein that is useful in the treatment or amelioration of one or more of the symptoms of diseases or disorders associated with caveolar endocytosis, PM microdomain formation, transmembrane signaling and integrin function, or in which caveolar endocytosis, PM microdomain formation, transmembrane signaling and integrin function is implicated, and a pharmaceutically acceptable carrier. Diseases or disorders associated with caveolar endocytosis, PM microdomain formation, transmembrane signaling and integrin function include, but are not limited to, inflammatory diseases and cancer. Pharmaceutical carriers suitable for administration of the compounds provided herein includes any such carriers known to those skilled in the art to be suitable for the particular mode of administration.

In addition, the compound may be formulated as the sole pharmaceutically active ingredient in the composition or may be combined with other active ingredients.

The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation, dry powder inhalers, or aerosols. In one embodiment, a compound as described above is formulated into a pharmaceutical composition using techniques and procedures well known in the art (see, e.g., Ansel Introduction to Pharmaceutical Dosage Forms, Fourth Edition 1985, 126).

In the compositions, effective concentrations of a compound or pharmaceutically acceptable derivative thereof is mixed with a suitable pharmaceutical carrier. The compound may be derivatized as the corresponding salt, ester, acetal, ketal, orthoesters hemiacetal, hemiketal, acid, base, solvate, or hydrate. The concentrations of the compound in the composition is effective for delivery of an amount, upon administration, that treats or ameliorates one or more of the symptoms of diseases or disorders associated with integrin function or in which integrin function is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems and then extrapolating to dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with integrin function or in which integrin function is implicated, as described herein.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compound exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. In certain embodiments, the compound of Formula I may be utilized with a carrier. Potential carriers may include alcohol, DMSO, serum album, and artificial lipid vesicles (e.g., Liposomes), which may or may not contain other lipids (e.g., phosphatidylcholine). This latter method may be particularly useful in certain embodiments where in vivo delivery via airways is utilized.

Derivatives of the compounds, such as pharmaceutically acceptable salts of the compounds may also be used in formulating effective pharmaceutical compositions.

Upon mixing or addition of the compound(s), the resulting mixture may be a solution, suspension, emulsion, or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Methods of Use of the Compounds and Compositions

Provided herein are methods to inhibit caveolar endocytosis, PM microdomain formation, transmembrane signaling and integrin function through contact of cells with a compound of Formula I.

In certain embodiments, the exposure of cells to a compound of Formula I results in an inhibition of caveolar endocytosis, PM microdomain formation, transmembrane signaling, and/or integrin function within exposed cells. Introduction of the composition can be made in vivo or in vitro and may include incubation or exposure of the cells to a pure compound of Formula I, or may instead include other compounds or solutions (e.g., water, buffers, antibodies, interleukins, fluorescently-labeled cellular components, alcohols, DMSO, serum album, liposomes, and/or lipids). Any cell type may be used, and may include fibroblasts, eosinophils, epithelials, ciliated, muscle, erythrocytes, leukocytes, neurons, oligodendrocytes, stem cells, as well as cancer cells from, for example, ovarian, small lung cell carcinomas, glioblastoma, and prostate tumors. A change or modulation to the aforementioned cellular functions may be determined through the comparison of cellular function within similar cells which have been left untreated, as a control, or exposed to an SL of known function, for example, C8-DE-LacCer.

In some embodiments, inhibition of cellular functions may include inhibition of one or more of the following: plasma membrane microdomain formation; integrin clustering and activation within plasma membrane microdomains; caveolar endocytosis, src kinase activity, superoxide production, and degranulation. In certain embodiments, the integrin inhibited by a compound of Formula I may include, but is not limited to, those listed in Table 1 (adapted from Faull, R. J. and Ginsberg, M. H., *J. Am. Soc. Nephrol* 1996, 7, 1091.). For example, treatment of HSFs with C8-LT-LacCer, inhibits β1-integrin, preventing caveolar endocytosis.

TABLE 1

The Integrin Family[a] (adapted from Faull, R. J. et al., J. Am. Soc. Nephrol. 1996, 7, 1091.)

| Integrin | Alternative Name(s) | Ligand(s) | Distribution |
|---|---|---|---|
| α1β1 | VLA-1, CD49a/CD29 | Collagen, laminin | Broad |
| α2β1 | VLA-2, CD49b/CD29 | Collagen, laminin | Broad |
| α3β1 | VLA-3, CD49c/CD29 | Laminin-5, fibronectin, collagen | Broad |
| α4β1 | VLA4, CD49d/CD29 | Fibronectin, VCAM-1 | Lymphocytes, muscle, monocytes/macrophages, neutral crest cells, fibroblasts |
| α5β1 | VLA-5, CD49e/CD29 | Fibronectin | Broad |
| α6β1 | VLA-6, CD49f/CD29 | Laminin, fertilin | Broad |
| α7β1 | VLA-7 | Laminin | unknown |
| α8β1 | VAL-8 | Firbronectin, vitronecting, tenascin | Neutral |
| α9β1 | VLA-9 | Tenascin | unknown |
| αvβ1 | | Fibronectin, cittronectin | Epithelial cells |
| αLβ2 | LFA-1, CD11a/CD18 | ICAM-1, ICAM-2, ICAM-3 | Leukocytes |

TABLE 1-continued

The Integrin Family[a] (adapted from Faull, R. J. et al., J. Am. Soc. Nephrol. 1996, 7, 1091.)

| Integrin | Alternative Name(s) | Ligand(s) | Distribution |
|---|---|---|---|
| αMβ2 | Mac-1, CD11b/CD18 | Fibrogen, IC3b, ICAM-1, factor X | Monocytes, granulocytes, natural killer cells, cytotoxic T lymphocytes |
| αXβ2 | p150, 95, CD11c/CD18 | Fibrinogen, IC3b | Monocytes, granulocytes, activated B lymphocytes |
| αIIbβ3 | gpIIb/IIIa | Fibrinogen, fibronectin, vWF, vittronectin | Platelets, megakaryocytes |
| αvβ3 | VnR | Fibrinogen, fibronectin, vWF, vittronectin, Thrombosponsin, osteoppontin, collagen | Endothelium, tumor cells |
| α6β4 | | Laminin-1, laminin-5 | Epithelial cells |
| αvβ5 | | Vitronectin, fibronectin | Carcinoma cells |
| αvβ6 | | Fibronectin | unknown |
| α4β7 | | VCAM-1, fibronectin, MadCAM-1 | Actibated B and T lymphocyes, monocytes/macrophages |
| αEβ7 | | E-cadherin | Intraepithelial lymphocytes |
| αvβ8 | | Vitronectin | unknown |

[a]VCAM-1, vascular cell adhesion molecule-1; ICAM, intercellular adhesion molecule; IC3b, Inactivated complement component C3; vWF, con Willebrand factor; MadCAM-1, mucosal addressin cell-adhesion molecule.

In another embodiment, the composition of Formula I can be used to treat, prevent, or ameliorate one or more symptoms of a disease associated with caveolar endocytosis, PM microdomain formation, transmembrane signaling, and/or integrin function in a mammal (e.g., a human, dog, pig, monkey, cat, mouse, rat, or horse). For example, inhibition of caveolar endocytosis could have significant effects on inflammatory responses, or the mobility of cancerous or precancerous cells. Diseases associated with an inflammatory response can include allergies, Alzheimer's, anemia, aortic valve stenosis, arthritis, cancer, congestive heart failure, fibromyalgia, fibrosis, heart attack, kidney failure, lupus, pancreatitis, psoriasis, stroke, and surgical complications. Caveolar endocytosis may also participate in the proliferation of various types of cancer (e.g., breast cancer, prostate cancer, skin cancer, lung cancer, leukemia, colon cancer, and Non-Hodgkin Lymphoma). Further applications of the compound of Formula I may include blocking the uptake and/or binding of particular pathogens by cells, as caveolae have been implicated in the uptake of certain viruses (e.g., SV40), toxins (e.g., chlolera toxin B subunit), fungi, bacteria, SLs, and albumins in various cell types.

In a further embodiment, the composition of Formula I may be used to treat, prevent, or ameliorate one or more symptoms of a disease associated with integrin function in a mammal. Diseases linked to integrin function may include Multiple Sclerosis (see, e.g., Sheremata W. A. et al., *CNS Drugs* 2005; 19(11), 909), prothrombotic risk (see, e.g., Vijayan, K. V and Bray, P. F., *Exp. Biol. Med.* 2006, 231(5), 505), ulcerative colitis (see, e.g., Ferraccioli, G. F. et al., *Eur. Rev. Med. Pharmacol., Sci.* 2006, 10(1), 37), and renal disease (see, e.g., Blattner, S. M. and Kretzler, M., *Curr Opin. Nephrol. Hypertens.* 2005, 14(4), 404).

In one embodiment of this disclosure, a compound of Formula I may be used to study cellular processes, for example, caveolar endocytosis. These lipids may be used to modulate plasma membrane microdomain formation and therefore the downstream processes reliant on this functionality. Inhibition may be initiated through exposure (e.g., contact, addition, etc) of cells to a compound of Formula I either in vitro or in vivo. In certain embodiments, additional components may be used in conjunction with the lipid to further explore cellular functions (e.g., antibodies, interleukins, fluorescently-labeled cellular components, and biological inhibitors of cellular processes). In some embodiments, a compound of Formula I may be used in conjunction with a test compound to determine if the test compound is capable of restoring an inhibited function (e.g., caveolar endocytosis or uptake of a pathogen) while in the presence of a compound of Formula I. Any appropriate cells may be used with a compound of Formula I, depending on the purpose of the study. For example, eosinophils may be used to study the role of PM microdomain formation in the inflammatory response, while skin fibroblasts may be used to investigate the role of this process on various endocytic events. In addition, a compound of Formula I might be particularly effective in modulating tumor cell motility and invasiveness since integrins bind to extracellular matrix proteins and cell surface ligands and are responsible for many types of cell adhesion events. For these studies, cancer cells from ovarian, small lung cell carcinomas, glioblastoma, and prostate tumors may be particularly useful.

EXAMPLES

Example 1

A Dominant Negative (DN) Lipid, C8-LT-LacCer, Inhibits Caveolar Endocytosis

Previous work has demonstrated that acute treatment of cells with exogenous GSLs (natural or synthetic; all with natural D-erythro (DE) stereochemistry, including C8-DE-LacCer) or elevation of cellular cholesterol dramatically and selectively stimulated caveolar endocytosis without affecting other endocytic mechanisms (see, e.g., Sharma, D. K. et al., *Molec. Biol. Cell* 2004, 15, 3114 and Sharma, D. K. et al., *Cancer Res.* 2005, 65, 1). Importantly, no stimulation was seen when cells were treated with other classes of lipids and stimulation was not due to degradation of the exogenous GSLs.

The non-natural (L-threo; LT) isomers of C8-LacCer and BODIPY-LacCer were synthesized. The latter was synthesized by the method detailed in Liu, Y., et al. *Chem. Phys. Lipids,* 2006, 142, 58 (referred to as Liu). C8-LT-LacCer was prepared through a modification of the methods used in Liu, where an activated for of octanoic acid was used in place of BODIPY-$C_5$-NHS. HSFs were then either untreated (Control) or treated for 30 min at 10° C. with D-erythro (DE) or L-threo (LT) C8-LacCer, and then pulse labeled with fluorescent albumin or anti-β1-integrin Fab (caveolar markers), Tfn (clathrin marker), dextran (fluid phase marker), or anti-IL2R Fab (for RhoA pathway). After 5 min at 37° C., cells were acid-stripped to remove non-internalized marker and images were acquired by fluorescence microscopy (A) and quantified (B). At least 20 cells for each condition were analyzed in multiple experiments. Bar, 10 μm.

Figure 2:
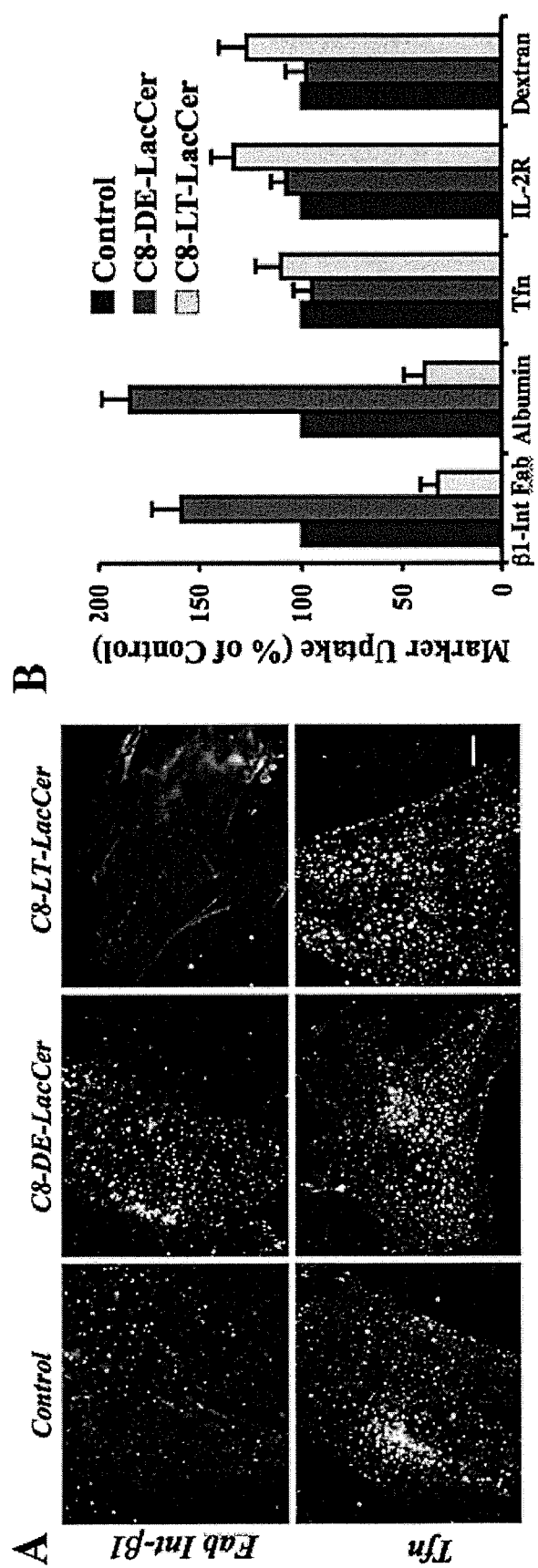
FIG. 2 demonstrates that the LT-isomer of C8-LacCer acts as a "dominant negative lipid," selectively inhibiting caveolar endocytosis in HSFs. HSFs were either untreated (Control) or treated for 30 min at 10° C. with D-erythro or L-threo-C8-LacCer, and then pulse labeled with fluorescent albumin or β1-integrin Fab (caveolar markers), Tfn (clathrin marker), dextran (fluid phase marker), or anti-IL2R Fab (for RhoA pathway). After 5 min at 37° C., cells were acid-stripped to remove non-internalized marker and images were acquired by fluorescence microscopy (A) and quantified (B). At least 20 cells for each condition were analyzed in multiple experiments. Bar, 10 µm.

The LT-lipid inhibited uptake of multiple caveolar markers in HSFs, as shown in FIG. 2; compare C8-LT-LacCer (yellow bars) to the corresponding DE isomer (red bars), which stimulated caveolar uptake as noted above. Furthermore, in contrast to BODIPY-DE-LacCer which is internalized via caveolae (see, e.g., Singh et al., *J. Biol. Chem.* 2006, in press), BODIPY-LT-LacCer was internalized primarily (~65-70%) by clathrin-dependent endocytosis (data not shown). This result is particularly significant because selective inhibition of this pathway may have important applications in basic studies of endocytosis and in blocking uptake of particular pathogens by cells.

Example 2

Inhibition of PM Microdomains and SV40 Binding

Figure 3:
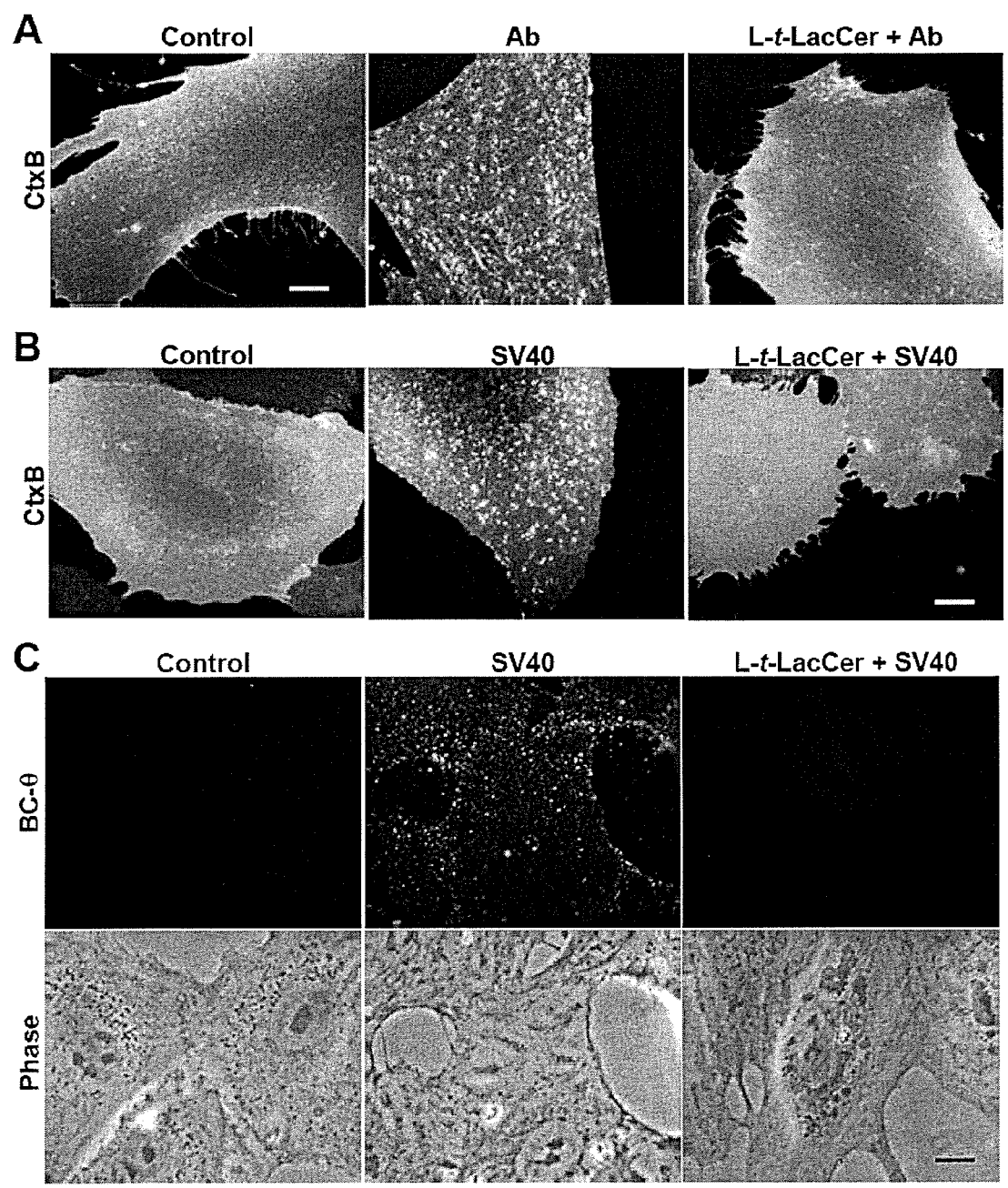
FIG. 3 demonstrates C8-LT-LacCer inhibition of PM domain formation. PM domains enriched in $GM_1$ ganglioside (A,B) or cholesterol (C) were visualized using fluorescent CtxB or BC-⊖, respectively. Clustering of these probes was induced using an anti-CtxB Ab or SV40. Note the inhibition of microdomain clustering when cells were pretreated with C8-LT-LacCer, compared to untreated control samples. (A), HSFs; (B,C) CV1 cells. Bars, 10 µm.

A potential mechanism for C8-LT-LacCer inhibition of caveolar endocytosis, namely disruption of PM microdomain formation, was explored. This mechanistic possibility was tested through incubation of cells with AF594-CtxB at 10° C. to label GM ganglioside at the PM, followed by an anti-Ctx-B IgG. This treatment caused the formation of numerous micron-sized clusters of Ctx-B at the PM which were not present in the absence of Ab (FIG. 3A, left vs. middle). Importantly, when cells were pretreated with LT-LacCer for 30 min at 10° C. prior to incubation with the labeled CtxB and crosslinking Ab, no clustering of PM domains was observed (FIG. 3A, right). No inhibition of domain formation was observed using C8-DE-LacCer; rather the DE isomer induced the formation of large domains enriched in $GM_1$ ganglioside and cholesterol, in the absence of a crosslinking Ab (see, e.g., Singh, R. D., et al., 2006, submitted).

CV1 cells were then incubated at low temperature with SV40 virus and it was found that this treatment induced the formation of PM domains enriched in $GM_1$ ganglioside and cholesterol, (FIG. 3B,C, left vs. middle) remarkably similar to the clustered microdomains induced by CtxB crosslinking (FIG. 3A). Interestingly, pretreatment of CV1 cells with C8-LT-LacCer prevented the SV40 induction of these PM domains (FIG. 3B,C, right panels). These results provide a potential explanation for the reduction in SV40 binding to CV1 cells since $GM_1$ ganglioside is a receptor for SV40 (see, e.g., Norkin, L. C. and Kuksin, D., *Virol. J* 2005, 3, 38; and Tsai, B. et al., *EMBO. J.* 2003, 22, 4346) and clustering of $GM_1$ may be required for maximal SV40 binding.

Together, these experiments demonstrate that the induction of PM domains by various treatments (crosslinking Abs or SV40) is prevented by C8-LT-LacCer. This modulation of PM domain organization may disrupt the selection of cargo for subsequent caveolar uptake.

Example 3

Figure 4:
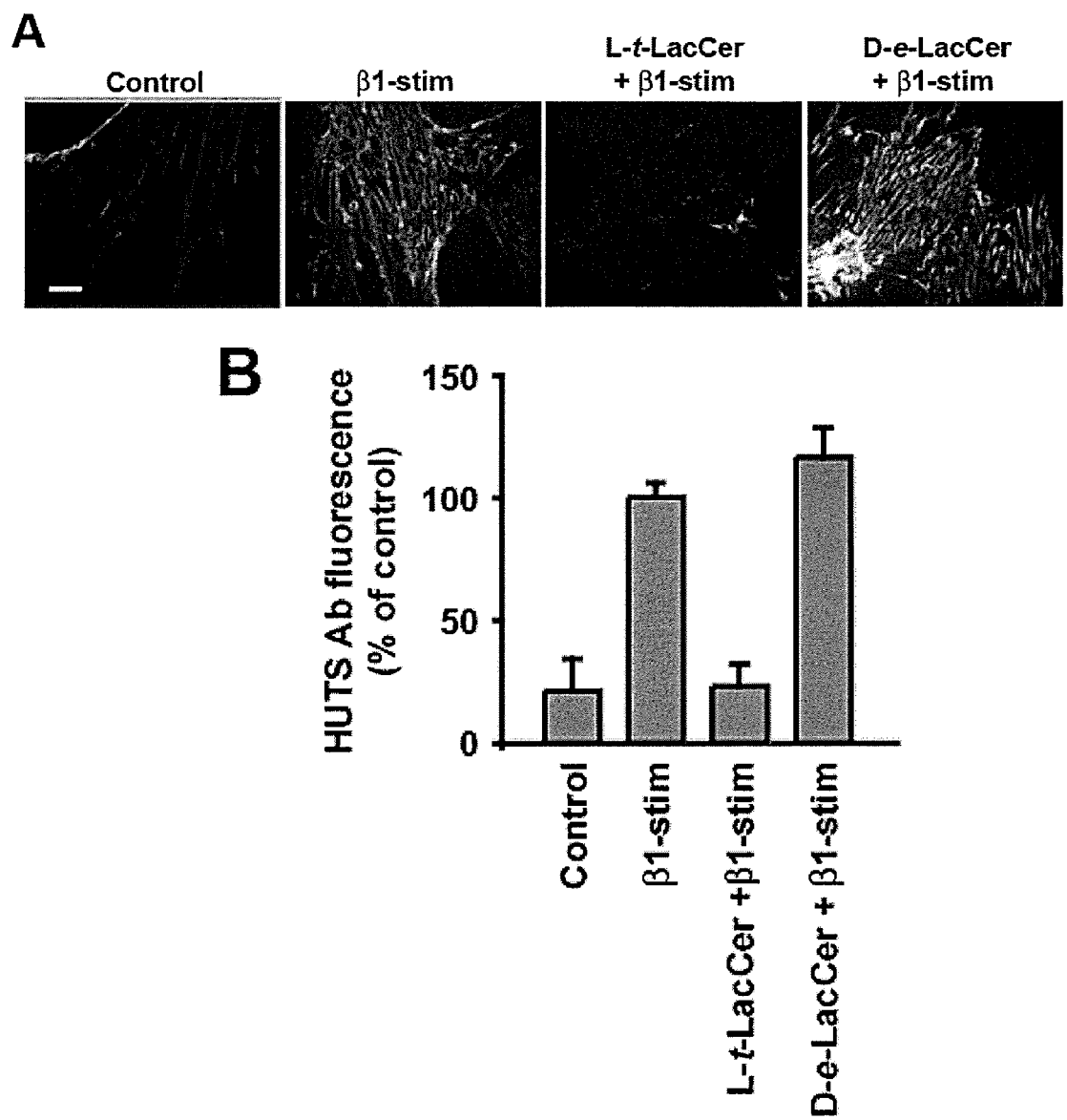
FIG. 4. demonstrates activation of β1-integrin and stimulation of src kinase is inhibited by C8-LT-LacCer.

Effect of C8-LacCer Stereoisomers on β1 Integrin Activation and src Phosphorylation A further mechanistic possibility by which C8-LT-LacCer might inhibit caveolar internalization is by disruption transmembrane signaling events required for endocytosis. Signaling through β1-integrin was studied because this integrin is internalized via caveolae in HSFs and other cell types (see Sharma, D. K. et al., *Cancer Res.* 2005, 65, 8233; and Upla, P. et al., *Mol. Biol. Cell* 2004, 15, 625), and because an early event following integrin activation is signaling through src, a kinase whose activity is required for caveolar endocytosis (see, e.g., Mineo, C. and Anderson, R. G., *Histochem. Cell Biol.* 2001, 116, 109; Sharma, D. K. et al., *Cancer Res.* 2005, 65, 8233; and Arias-Salgado, E. G. et al., *Proc. Natl. Acad. Sci. U.S.A.* 2003, 100, 13298). The first examination involved the activation of β1-integrin in HSFs following crosslinking with a stimulatory Ab (β1-stim Ab) using the HUTS-4 Ab which only binds to β1-integrins in their activated conformation (see, e.g., Luque, A. et al., *J. Biol. Chem.* 1996, 271, 11067). Treatment with the stimulatory Ab dramatically increased HUTS binding (FIG. 4), while pretreatment with C8-LT-LacCer prior to incubation with β1-stim Ab reduced HUTS binding to levels seen in untreated control cells. In contrast, when C8-DE-LacCer was used, the Ab-induced activation of β1-integrin was not inhibited. When C8-LT-LacCer was incubated with HSFs in the absence of β1-stim Ab, no increase in HUTS binding was seen (data not shown). This is in contrast to C8-DE-LacCer which activated β1-integrin in the absence of the β1-stim Ab, to a similar extent as when the Ab was used alone (data not shown).

Figure 5:
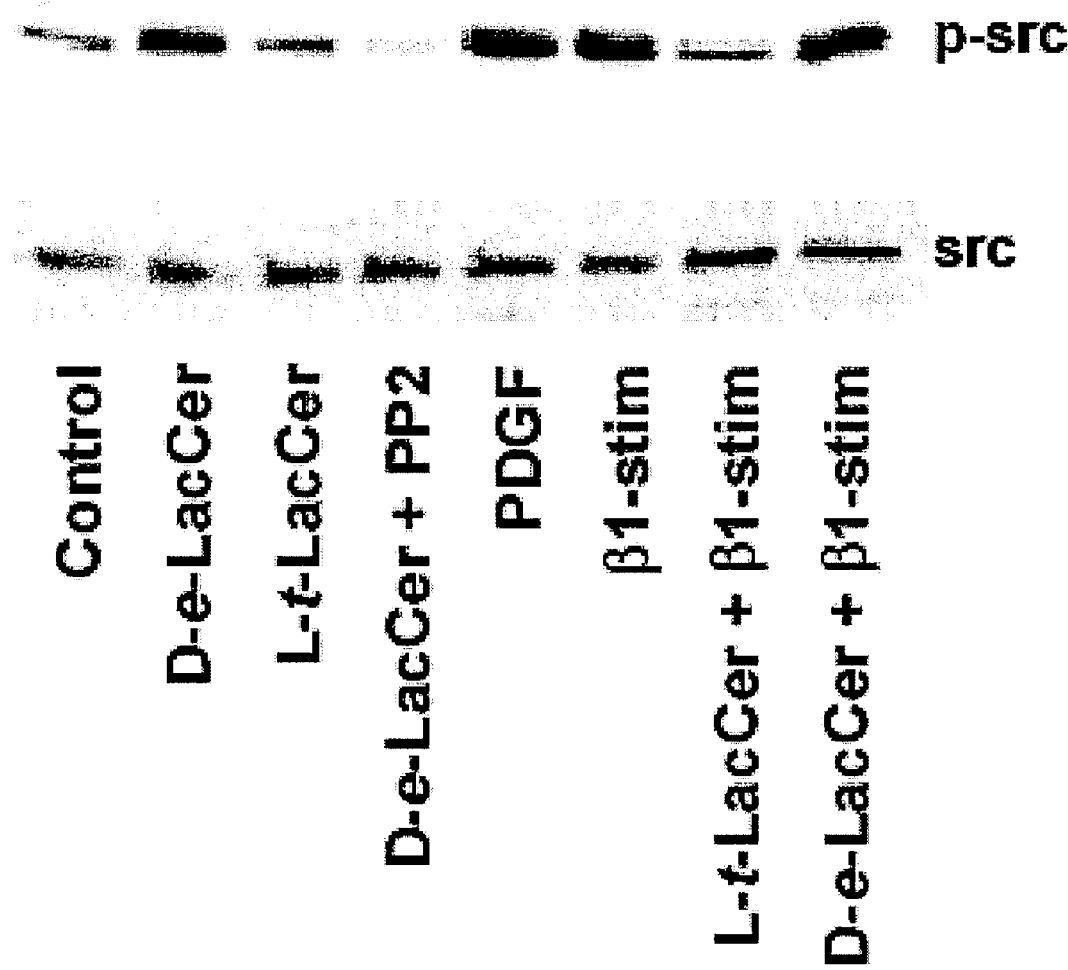
FIG. 5 demonstrates the effect of C8-LacCer stereoisomers on src activation. HSFs were treated with C8-DE-LacCer (±PP2), C8-LT-LacCer, PDGF, or with β1 stim Ab±LacCer isomers. Samples were warmed for 30 sec at 37° C., lysed, and the cell lysates blotted for src and phosphor-Src (Y416).

Since β1 integrins have been shown to activate src kinases and src phosphorylation is required for caveolar endocytosis (see, e.g., Sharma, D. K. et al., *Mol. Biol. Cell* 2004, 15, 3114; and Arias-Salgado, E. G. et al., *Proc. Natl. Acad. Sci. U.S.A.* 2003, 100, 13298), the effect of C8-LT-LacCer treatments on these processes were also examined. Cells were incubated for 30 min at 10° C.± the LacCer stereoisomers and/or the β1-stim Ab followed by a 30 sec incubation at 37° C. Cell lysates were then immunoblotted for src and phospho-(Y416) src. Src kinase was activated (phosphorylated at Y416) by treatment with C8-DE-LacCer to a level similar as that seen with the stimulating antibody and this activation could be blocked by the src inhibitor, PP2 (FIG. 5). In contrast, little or no src activation was observed upon treatment with C8-LT-LacCer. Furthermore, pretreatment of cells with C8-LT-LacCer inhibited src phosphorylation induced by the β1-stim Ab, while pretreatment with C8-DE-LacCer did not significantly affect src phosphorylation in response to β1-stim (data not shown).

Example 4

Effect of C8-DE-LacCer on Eosinophils

Human eosinophils were purified from normal individuals or patients with mild allergy by Percoll density gradient centrifugation and magnetic cell sorting using MACS anti-CD16 microbeads as described by Hansel T. T., et al., *J. Immunol. Methods* 1991, 145, 105. Briefly, after peripheral blood was overlaid on an isotonic Percoll solution (1.084 g.ml, Sigma), the blood was centrifuges at 1000×g for 30 min at 4° C. Mononuclear cells at the interface were removed, and erythrocytes in sediment were lysed by two cycles of hypotonic water lysis. Isolated granulocytes were washed twice in PIPES buffer (25 mM PIPES, 50 mM NaCl, 5 mM KCl, 25 mM NaOH, 5.4 mM glucose, pH 7.4) containing 1% alpha calf serum (HyClone Laboratories; Logan, Utah). Cells were then incubated with equal volume of anti-CD16 mAb MACS microbeads for 60 min at 4°C. with occasional gentle mixing. After 60 min of incubation on ice, cells were loaded onto the separation column positioned in the MACS magnetic field. Cells were eluted three times with 5 ml of PIPES buffer with 1% DCS. The purity of eosinophils counted by Randolph's stain was >98%. The contaminating cells were neutrophills, and no mononuclear cells or basophils were present. Purified eosinophils were used immediately for experiments.

Superoxide anion generation and degranulation by human eosinophils were used as readouts of eosinophils functions in response to proteases or synthetic PAR activating peptides. Generation of superoxide by eosinophils was measured by superoxide dismutase-inhibitable reduction of cytochrome c as previously described with slight modifications. Freshly isolated eosinophils were washed and resuspended in Hank's balanced salt solution (HBSS) with 25 mM HEPES and 0.01% gelatin (Sigma) and 100 mM cytochrome c at $5\times10^5$ cells/ml. Cell suspension (100 µl) was dispensed onto the wells of 96-well tissue culture plates, followed by 100 µl of serial dilution of C8-DE-LacCer or medium alone. Immediately after addition of stimuli, the reaction wells were measured for absorbance at 550 nm in a microplate autoreader (Thermomax, Molecular Devices, Menlo Park, Calif.), followed by repeated readings. Between absorbance measurements, the plate was incubated at 37° C. After incubation and repeated measurements of superoxide production at 37° C. and 5% $CO_2$ for 4 h, cell-free supernatants from 96-well tissue culture plates were collected, and stored at −20° C. until assayed for eosinophils degranulation. To quantitate eosinophils degranulation, the concentrations of eosinphil-derived neutrotoxin (EDN) in the sample supernatants were measure by specific RIA.

C8-DE-LacCer induces adhesion of eosinophils to tissue culture wells. Eosinophils incubated with C8-DE-LacCer were flattened and showed spindle shape with many pseudopods, suggesting integrin-mediated cellular adhesion. A large quantity of superoxide was produced by eosinophils stimulated with C8-DE-LacCer but not those incubated with medium alone. Furthermore, a granule protein, EDN, was released into supernatants by eosinophils incubated with C8-DE-LacCer. Given the effects of C8-DE-LacCer on eosinophils superoxide anion generation and adhesion, it is anticipated that C8-LT-LacCer may have inhibitory effects on some of these processes.

Example 5

Structural Requirements for GSL Internalization

To define the molecular features of GSL analogs and their ability to selectively internalize by caveolar endocytosis, the structure of the natural D-erythro-LacCer compound was modified (Singh, R. D., et al. *Mol. Biol. Cell,* 2003, 14, 3254). The modifications included those to the structure of the fluorescent lipid through variations to its carbohydrate headgroup, chain length of the sphingosine base, or chain length of the fluorescent fatty acid (see FIG. 6). Tests were designed to test initial internalization and sensitivity to inhibitor treatments.

Figure 6:
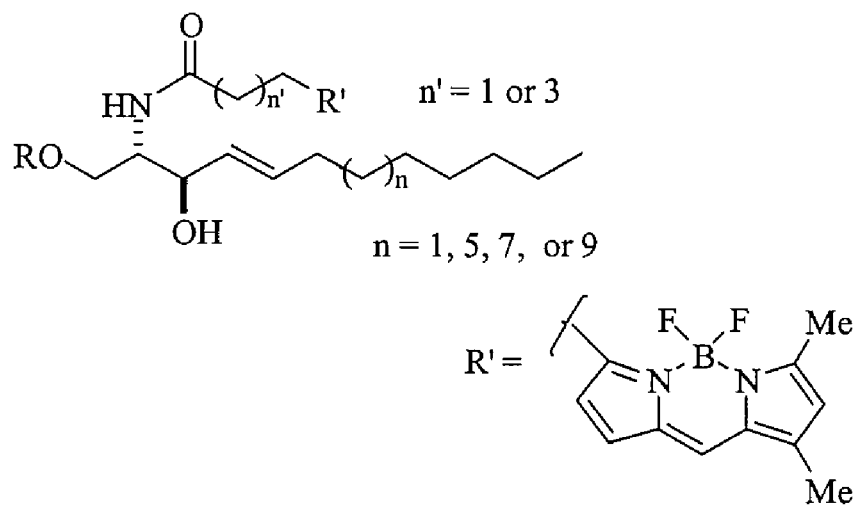
FIG. 6 structures of fluorescent lipid analogs. (A) various headgroups (R) were attached to BODIPY-ceramide, resulting in BODIPY-GalCer, -LacCer, -MalCer, -globoside, -sulfatide, or $GM_1$. BODIPY-LacCer analogs were also synthesized using various chain length ($C_{12}$, $C_{16}$, $C_{18}$, or $C_{20}$) sphingosines of BODIPY-fatty acids ($C_3$ vs. $C_5$ spacer). Fluorescent LacCer bearing an NBD-fatty acid (see B) in place of the BODIPY-fatty acid was also synthesized. (B) Structure of the D-isomer of NBD-labeled PC, a glycerolipid.
Figure 6:
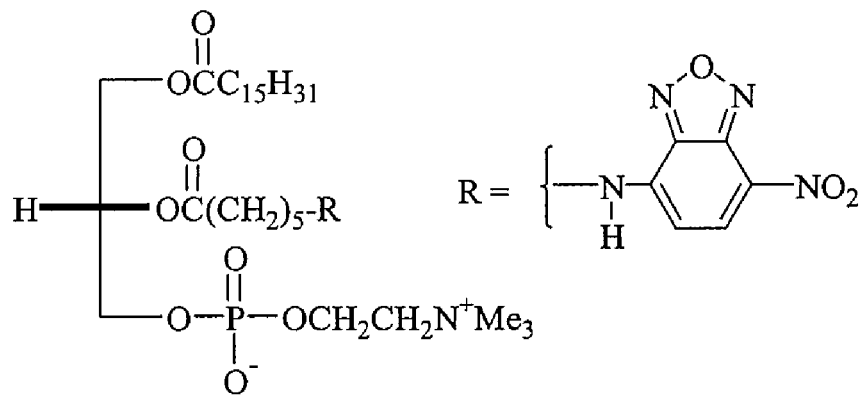

To investigate the structural determinants of GSLs that result in selective internalization via caveolae, the structure of the fluorescent GSL analogs were systematically varied (see FIG. 6) and examined to determine the effect of these variations on the mechanism of analog internalization. To examine the significance of the carbohydrate head group, the fluorescent analogs of GalCer, globoside, $GM_1$, LacCer, MalCer, and sulfatide were used. For each of these fluorescent GSL analogs, the fluorescent fatty acid and sphingosine base were identical (n'=3, n=7; FIG. 6A). Rat fibroblasts (RFs) were incubated with each analog in the presence or absence of various inhibitors to differentiate clathrin-dependent from clathrin-independent endocytosis, and the amount of internalization (at 5 min) was quantified by image analysis. The internalization of each GSL analog (GalCer, globoside, $GM_1$, LacCer, MalCer, and sulfatide) was substantially inhibited by nystatin (but not by chlorpromazine (CPZ)), similar to BODIPY-LacCer (see Table 2), indicating that the specific carbohydrate headgroup structure or the stereochemistry of the glycosidic linkage in the disaccharide moiety of the GSL does not play a significant role in selective internalization of these GSLs by the clathrin-independent, caveolar mechanism.

A control experiment was carried out exactly as above, except that BODIPY-LacCer was introduced into cells from an ethanolic solution rather than from a BSA complex. As seen in Table 2, virtually identical results were obtained when the LacCer analog was delivered to RFs using BSA vs. ethanol injection, indicating that the BSA carrier did not influence the LacCer uptake mechanism.

Furthermore, the importance of hydrophobicity on the mechanism of GSL endocytosis was examined. For these studies, the BODIPY-LacCer analogs that were used varied the chain length of the sphingosine base ($C_{12}$ to $C_{20}$), or fatty acid ($C_3$ vs. $C_5$ spacer) (n=1, 5, 7, or 9; n'=1 or 3; FIG. 6A). Endocytosis of the series of LacCer analogs was studied in RFs as above, but surprisingly none of the modifications in chain length affected the mechanism of LacCer internalization. To investigate the possible influence of the BODIPY fluorophore, the internalization of NBD-labeled LacCer was studied, and it was found that its internalization was nystatin-inhibitable and CPZ-insensitive (see Table 2), similar to our findings for BODIPY-LacCer (and other BODIPY-GSLs). This demonstrated that the fluorophore (NBD vs. BODIPY) had no apparent influence on the internalization mechanism.

Finally, a comparison between NBD-LacCer and NBD-D-PC (see FIG. 6B) was made to study the possible influence of the lipid backbone (ceramide vs. glycerol) on the internalization mechanism. As shown in Table 2, the endocytosis of NBD-D-PC was found to be predominantly CPZ-inhibitable, suggesting that unlike LacCer, its uptake occurred largely by clathrin-dependent endocytosis.

These structural studies suggest that GSL uptake via caveolae is not selective for a specific carbohydrate headgroup, acyl chain hydrophobicity, or fluorophore substitution; however, comparison with the uptake of NBD-D-PC suggests that the ceramide core of GSLs may play an important role in caveolar endocytosis of GSLs. For further experimental details, see, e.g., Marks, D. L. et al., *Methods* 2005, 36, 186-195; and Singh, R. D., et al., *Curr. Prot. Cell. Bio.* 2006, in press).

TABLE 2

Inhibition of lipid analog endocytosis by different biochemical treatments in rat fibroblasts

| Fluorescent lipid analog | Clathrin-independent internalization | | Clathrin-dependent internalization | |
|---|---|---|---|---|
| | Nystatin % | Genistein % | Chlorpromazine % | $K^+$-depletion % |
| BODIPY-GalCer | 71.9 ± 9.5 | ND | 10.5 ± 2.8 | ND |
| BODIPY-LacCer | 75.1 ± 6.8 | 73.9 ± 4.1 | 9.3 ± 1.7 | 10.4 ± 1.3 |
| BODIPY-MalCer | 76.7 ± 8.2 | ND | 9.2 ± 1.9 | ND |
| BODIPY-Globoside | 82.6 ± 10.5 | 82.0 ± 4.5 | 0.7 ± 0.1 | 7.0 ± 0.8 |
| BODIPY-Sulfatide | 78.2 ± 7.6 | 73.6 ± 9.7 | 9.1 ± 2.2 | ND |
| BODIPY-$GM_1$ | 74.7 ± 8.2 | 69.9 ± 8.9 | 8.8 ± 1.2 | 11.6 ± 2.1 |
| NBD-LacCer | 75.6 ± 6.7 | ND | 15.1 ± 2.4 | ND |
| NBD-D-PC | 20.4 ± 4.4 | ND | 71.3 ± 8.5 | ND |

Example 6

Effect of C8-LT-LacCer on SV40 Infection and Binding

Figure 7:
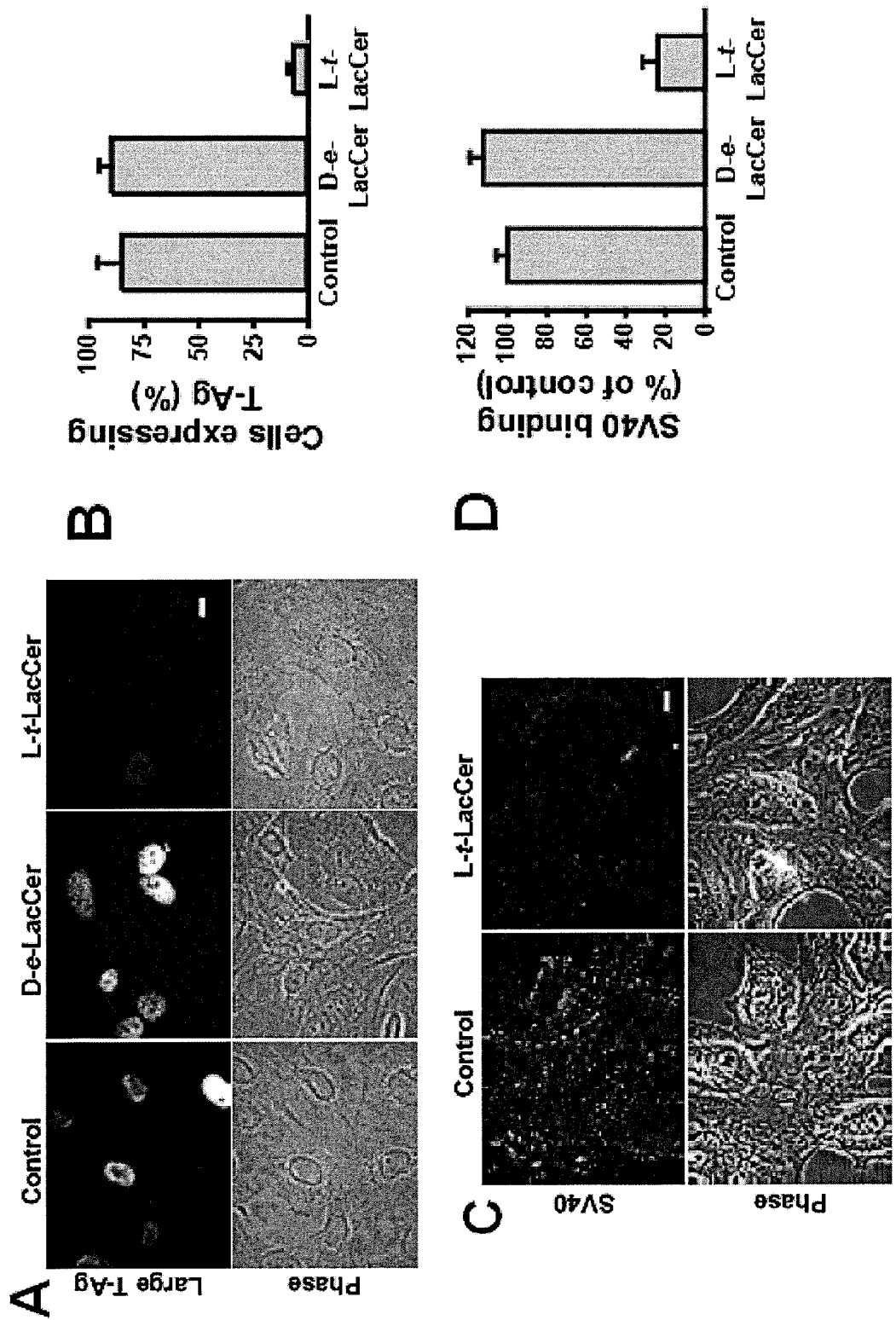
FIG. 7 demonstrates inhibition of SV40 infection and binding by C8-LT-LacCer. (A, B) CV1 cells were incubated LacCer stereoisomers for 30 min at 10° C., and then coincubated for 1 hr at 10° C. with SV40 virus (MOI=15). Samples were washed, incubated for 40 hrs in complete medium, fixed, permeabilized, and stained for the Large T antigen. Values in (B) are mean ±SD (n≧50 cells/condition; three independent experiments). (C, D) CVI cells were treated with SV40 for 1 hr as in (A,B) and SV40 binding to live cells was detected using anti-SV40 VP1 MAb. Values in D are mean ±SD (n≧20 cells from two independent experiments). Bars, 10 µm.

The effect of C8-LT-LacCer treatment on SV40 infection in monkey CV1 cells was examined as endocytosis of this virus has been extensively characterized in this cell type and shown to occur via caveolae (Pelkman, L., et al. *Nature Cell Biol.* 2001, 3, 473; Anderson, H. A., et al., *Mol. Biol. Cell* 1996, 7, 1825; Stang, E., et al. *Mol. Biol. Cell* 1997, 8, 47.) CV1 cells were pretreated with the LacCer stereoisomers and SV40 at low temperature, washed, and shifted to 37° C. for 14 hrs. Pretreatment of cells with C8-LT-LacCer dramatically reduced the vial infection as monitored by the expression of the large T antigen, while C8-DE-LacCer had no effect relative to untreated control samples (see FIG. 7A, B).

Since inhibition of SV40 infection by C8-LT-LacCer could result from effects on virus binding as well as endocytosis, we also studied the effect of C8-LT-LacCer on SV40 binding. Cells were treated with the C8-LT-LacCer isomer and SV40 at low temperature, washed, and then incubated with a monoclonal antibody to the SV40 major capsid protein VP1. C8-LT-LacCer inhibited SV40 binding to CV1 cells by about 80% (see FIG. 7C, D).

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating one or more symptoms of a disease associated with SV40 infection in a mammal, the method comprising administering to the mammal a therapeutically effective amount of a compound:

C8-LT-LacCer or a pharmaceutically acceptable salt form thereof,
thereby treating or ameliorating one or more of the symptoms of the disease associated with infection by SV40 in the mammal.

2. The method any of claim 1, wherein said mammal is a human.

3. A method of inhibiting caveolar endocytosis in a cell, comprising contacting the cell with a compound:

C8-LT-LacCer or a pharmaceutically acceptable salt form thereof.

4. The method of claim 3, wherein the contacting is done in vitro.

* * * * *

UNITED STATES PATENT AND TRADEMARK OFFICE
CERTIFICATE OF CORRECTION

| | |
|---|---|
| PATENT NO. | : 8,263,576 B2 |
| APPLICATION NO. | : 11/839024 |
| DATED | : September 11, 2012 |
| INVENTOR(S) | : Richard E. Pagano et al. |

Page 1 of 1

It is certified that error appears in the above-identified patent and that said Letters Patent is hereby corrected as shown below:

Column 28, line 28 (Claim 2), please delete "any of" and insert --of-- therefor.

Signed and Sealed this
Fifth Day of February, 2013

Teresa Stanek Rea
*Acting Director of the United States Patent and Trademark Office*